US008481518B2

(12) United States Patent
Wood

(10) Patent No.: US 8,481,518 B2
(45) Date of Patent: Jul. 9, 2013

(54) QUATERNARY ANTIMUSCARINIC COMPOUNDS FOR THE TREATMENT OF BLADDER DISEASES

(75) Inventor: Ronald W. Wood, Rochester, NY (US)

(73) Assignee: University of Rochester, Rochester, NY (US)

(*) Notice: Subject to any disclaimer, the term of this patent is extended or adjusted under 35 U.S.C. 154(b) by 1721 days.

(21) Appl. No.: 10/542,501

(22) PCT Filed: Jan. 15, 2004

(86) PCT No.: PCT/US2004/000961
§ 371 (c)(1),
(2), (4) Date: Jan. 10, 2006

(87) PCT Pub. No.: WO2004/064789
PCT Pub. Date: Aug. 5, 2004

(65) Prior Publication Data
US 2006/0154951 A1 Jul. 13, 2006

Related U.S. Application Data

(60) Provisional application No. 60/441,391, filed on Jan. 16, 2003.

(51) Int. Cl.
*A61K 31/33* (2006.01)
*A61K 31/00* (2006.01)
(52) U.S. Cl.
USPC ..................... 514/183; 514/211.01
(58) Field of Classification Search
USPC ........................................... 514/183
See application file for complete search history.

(56) References Cited

U.S. PATENT DOCUMENTS

| | | | |
|---|---|---|---|
| 2,648,667 A | 8/1953 | Sternbach | |
| 4,467,095 A | 8/1984 | Treves et al. | |
| 5,001,160 A | 3/1991 | McPherson et al. | |
| 5,236,956 A * | 8/1993 | Sjogren et al. | 514/617 |
| 5,552,407 A | 9/1996 | Wood et al. | |
| 5,610,163 A | 3/1997 | Banholzer et al. | |
| 5,654,314 A | 8/1997 | Banholzer et al. | |
| 5,770,738 A | 6/1998 | Banholzer et al. | |
| 5,779,661 A * | 7/1998 | Stephen et al. | 604/21 |
| 5,821,249 A | 10/1998 | Wood et al. | |
| 5,939,426 A * | 8/1999 | McCullough | 514/290 |
| 6,063,808 A * | 5/2000 | Fabiano et al. | 514/424 |
| 6,110,972 A * | 8/2000 | Fabiano et al. | 514/643 |
| 6,124,354 A * | 9/2000 | Åkerblom et al. | 514/530 |
| 6,171,298 B1 * | 1/2001 | Matsuura et al. | 604/891.1 |
| 6,183,461 B1 * | 2/2001 | Matsuura et al. | 604/502 |
| 6,204,285 B1 * | 3/2001 | Fabiano et al. | 514/424 |
| 6,482,837 B1 | 11/2002 | Wood | |
| 6,573,282 B1 | 6/2003 | Yaksh et al. | |
| 6,696,462 B2 | 2/2004 | Eickmeier et al. | |
| 6,974,820 B2 * | 12/2005 | Aberg | 514/278 |
| RE39,820 E | 9/2007 | Banholzer et al. | |
| 2006/0160887 A1* | 7/2006 | Yamagata et al. | 514/431 |

FOREIGN PATENT DOCUMENTS

| | | |
|---|---|---|
| WO | WO 98/00133 | 1/1998 |
| WO | WO 98/00138 | 1/1998 |
| WO | WO 0245711 A1 * | 6/2002 |

OTHER PUBLICATIONS

Disse et al. (Life Sciences, 1993, 52/5-6:537-544).*
Deaney et al., J Neurol Neurosurg Psychiatry, abstract, 1998, 65:957-958.*
Walter et al., Neurourology and Urodynamics, 18:447-453, 1999.*
Kuo, H.C., J. Formos. Med. Assoc., (May 2001), 100(5), 309-14 (abstract).*
Chuang et al., Journal of Urology, (Oct. 2009), 182(4), 1393-400.*
"Anticholinergic Therapy: The State of the Art. Proceedings of a Symposium Held in Stratford-Upon Avon Sep. 8-9, 1986," Higgenbottam et al., eds., *Postgrad. Med. J.* 63(Suppl 1):1-86 and Poster Abstracts and Discussion 63(Suppl 1):1A-31A (1987).
Autret et al., "Plasma Levels of Oxybutynine Chloride in Children," *Eur. J. Clin. Pharmacol.* 46:83-85 (1994).
Barbalias, G.A., "Interstitial Cystitis: Bladder Training with Intravesical Oxybutynin," *J. Urol.* 163:1818-1822 (2000).
Brendler et al., "Topical Oxybutynin Chloride for Relaxation of Dysfunctional Bladders," *J. Urol.* 141:1350-1352 (1989).
Brown et al., "Proceedings of the National Institute of Diabetes and Digestive and Kidney Diseases International Symposium on Epidemiologic Issues in Urinary Incontinence in Women," *Am. J. Obstet. Gynecol.* 188:S77-S88 (2003).
Chen et al., "Pulmonary Effects of the Cocaine Pyrolysis Product, Methylecgonidine, in Guinea Pigs," *Life Sciences* 56(1):7-12 (1995).
Davilla, G.W., "Advances in Anticholinergic Therapy Delivery Systems," *Urology Times*, pp. 1-2 (Jun. 2002).
Disse et al., "Ba 679 BR, A Novel Long-Acting Anticholinergic Bronchodilator," *Life Sciences* 52:537-544 (1993).
Disse et al., "Tiotropium (Spiriva™): Mechanistical Considerations and Clinical Profile in Obstructive Lung Disease," *Life Sciences* 64(6/7):457-464 (1999).
Eichel et al., "Assessment of Murine Bladder Permeability with Fluorescein: Validation With Cyclophosphamide and Protemine," *Urology* 58(1):113-118 (2001).
El-Fawal et al., "Airway Smooth Muscle Relaxant Effects of the Cocaine Pyrolysis Product, Methylecgonidine," *J. Pharm. Exp. Ther.* 272(3):991-996 (1995).
Gearien, J.E., "Cholinergics, Acetylcholinesterases, and Antispasmodics," Foye, W.O., eds., *Principles of Medicinal Chemistry*, Lean and Febiger, Philadelphia, PA, Chapter 15, pp. 323-341 (1989).
Franstz et al., "Implementing an Incontinence Management Protocol in Long-Term Care," *J. Gerontological Nursing* 29(8):46-53 (2003).
Heller et al., "Muscarinic Receptor Agonists and Antagonists," Goodman and Gilman, *The Pharmacological Basis of Therapeutics*, 10th Edition, Hardman et al., eds., McGraw-Hill, Chapter 7, pp. 155-173 (2000).

(Continued)

*Primary Examiner* — My-Chau T Tran
(74) *Attorney, Agent, or Firm* — LeClairRyan, a Professional Corporation

(57) ABSTRACT

The present invention relates to a method for treating bladder disease, including urinary incontinence, which involves intravesical administration of quaternary antimuscarinic compounds having longer duration of effect and fewer side effects than standard treatments.

32 Claims, No Drawings

OTHER PUBLICATIONS

Green et al., "Urinary Incontinence in Subacute Care—A Retrospective Analysis of Clincal Outcomes and Costs," *MJA* 178:550-553 (2003).
Greenfield et al., "The Use of Intravesical Oxybutynin Chloride in Children with Neurogenic Bladder," *J. Urol.* 146:532-534 (1991).
Gross, H.J., "Ipratropium Bromide," *New. Eng. J. Med.* 319:486-494 (1988).
Hay-Smith et al., "Anticholinergic Drugs Versus Placebo for Overactive Bladder Syndrome in Adults," *Cochrane Database Syst. Rev.* 3:CD003781 (2002) (Abstract).
Hogan, D.B., "Revisiting the O Complex: Urinary Incontinence, Delirium and Polypharmacy in Elderly Patients," *Can. Med. Assoc. J.* 157(8):1071-1077 (1997).
Hu et al., "Estimated Economic Costs of Overactive Bladder in the United States," *Urology* 61(6):1123-1128 (2003).
Krishnan, K.R., "A Double-Blind, Randomized, Placebo-Controlled, Parallel Group, Multicenter Study of Intravesical Oxybutynin," *Neurourol. And Urodyn.* 15:307-308 (1996) (Abstract #32).
Langtry et al., "Terodiline. A Review of its Pharmacological Properties, and Therapeutic Use in the Treatment of Urinary Incontinence," *Drugs* 40(5):748-761 (1990).
Madersbacher et al., "Control of Detrusor Hyperreflexia by the Intravesical Instillation of Oxybutynine Hydrochloride," *Paraplegia* 29:84-90 (1991).
Martin et al., "Pyrolysis and Volatilization of Cocaine," *J. Anal. Toxicol.* 13:158-162 (1989).
Norman et al., "Tiotropium Bromide, Treatment of COPD Bronchodilator Muscarinic Antagonist," *Drugs of the Future* 25(7):693-699 (2000).
Olesen et al., "Calcitonin Gene-Related Peptide Receptor Antagonist BIBN 4096 BS for the Acute Treatment of Migraine," *N. Engl. J. Med.* 350(11):1104-1110 (2004).
Pietzko et al., "Influences of Trospium Chloride and Oxybutynin on Quantitative EEG in Healthy Volunteers," *Eur. J. Clin. Pharmacol.* 47:337-343 (1994).
Scheidweiler et al., "Pharmacokinetics and Pharmacodynamics of Methylecgonidine, a Crack Cocaine Pyrolyzate," *J. Pharm. Exp. Ther.* 307(3):1179-1187 (2003).
Sessions et al., "Continuous Bladder Infusion Methods for Voiding Function in the Ambulatory Mouse," *Urology* 60(4):707-713 (2002).
Shih et al., "Labor Costs Associated with Incontinence in Long-Term Care Facilities," *Urology* 62(3):442-446 (2003).
Takahashi et al., "Effect of Ba 679 BR, A Novel Long-Acting Anticholinergic Agent, On Cholinergic Neurotransmission in Guinea Pigs and Human Airways," *Am. J. Resp. Crit. Care Med.* 150:1640-1645 (1994).
Thuroff et al., "Randomized, Double-Blind, Multicenter Trial on Treatment of Frequency, Urgency and Incontinence Related to Detrusor Hyperactivity: Oxybutynin Versus Propantheline Versus Placebo," *J. Urol.* 145:813-817 (1991).
Ukimura, O., "Effects of Intravesically Administered Anticholinergics, β-Adrenergic Stimulant and α-Adrenergic Blocker on Bladder Function in Unanesthetized Rats," *Tohoku J. Exp. Med.* 170:251-260 (1993).
Weese et al., "Intravesical Oxybutynin Chloride: Experience With 42 Patients," *Urology* 41:527-530 (1993).
Willetts et al., "Effects of Methylecgonidine on Acetylcholine-Induced Bronchoconstriction and Indicators of Lung Injury in Guinea Pigs," *Life Sciences* 57(15):225-230 (1995).
Witek, T.J. Jr., "Anticholinergic Bronchodilators," *Respiratory Clinica of North America* 5:521-536 (1999).
Wood et al., "Automated Noninvasive Measurement of Cyclophosphamide-Induced Changes in Murine Voiding Frequency and Volume," *J. Urol.* 165:653-659 (2001).
Wood et al., "Generation of Stable Test Atmospheres of Cocaine Base and Its Pyrolyzate, Methylecgonidine, and Demonstration of Their Biological Activity," *Pharmacology, Biochemistry & Behavior* 55(2):237-248 (1996).
Wood et al., "Uroflow in Murine Urethritis," *Research Insights into Interstitial Cystitis: A Basic and Clinical Science Symposium*, Alexandria, VA, Oct. 30-Nov. 1, 2003; co-presented by the National Institute of Diabetes and Digestive and Kidney Diseases and the Interstitial Cystitis Association (Abstract and Poster Presentation) (2 pp.).
Abood, "The Psychotomimetic Glycolate Esters," in Burger, ed., *Drugs Affecting the Central Nervous System* vol. 2, Chapter 4, New York: Marcel Dekker, Inc., pp. 127-167 (1968).
Abood, "Anticholinergics," Chap 15 in *Psychotropic Agents, Part III: Alcohol and Psychomimetics, Psychotropic Effects of Central Acting Drugs*, F. Hoffmeister et al., eds., Springer-Verlag, Berlin pp. 331-347 (1982).
Baumgold et al., "Chemical Factors Influencing the Psychotomimetic Potency of Glycolate Esters," *Life Sciences* 17:603-612 (1975).
Baumgold et al., "Studies on the Relationship of Binding Affinity to Psychoactive and Anticholinergic Potency of a Group of Psychotomimetic Glycolates," *Brain Research* 124:331-340 (1977).
Bonner et al., "Identification of a Family of Muscarinic Acetylcholine Receptor Genes," *Science* 237:527-532, Erratum 1556, 1628 (1987).
Bonner et al., "Cloning and Expression of the Human and Rat m5 Muscarinic Acetylcholine Receptor Genes," *Neuron* 1:403-410 (1988).
Brown, "Atropine, Scopolamine, and Related Antimuscarinic Drugs," in Goodman et al., eds., *The Pharmacological Basis of Therapeutics*, Eighth Edition, New York: Macmillan Publishing Co., pp. 150-165 (1990).
Buckley et al., "Antagonist Binding Properties of Five Cloned Muscarinic Receptors Expressed in CHO-K1 Cells," *Molecular Pharmacology* 35:469-476 (1989).
Carroll et al., "Probes for the Cocaine Receptor. Potentially Irreversible Ligands for Dopamine Transporter," *J. Med. Chem.* 35:1813-1817 (1992).
Carter et al., Analogues of Oxybutynin. Synthesis and Antimuscarinic and Bladder Activity of Some Substituted 7-Amino-1-hydroxy-5-heptyn-2-ones and Related Compounds, *J. Med. Chem.* 34:3065-3074 (1991).
Cereda et al., "Synthesis and Biological Evaluation of New Antimuscarinic Compounds with Amidine Basic Centers. A Useful Bioisosteric Replacement of Classical Cationic Heads," *J. Med. Chem.* 33:2108-2113 (1990).
Comer et al., "Clocinnamox: A Novel, Systemically-Active, Irreversible Opioid Antagonist," *The Journal of Pharmacology and Experimental Therapeutics* 262(3):1051-1056 (1992).
Connor et al., "Early Cystometrograms Can Predict the Response to Intravesical Instillation of Oxybutynin Chloride in Myelomeningocele Patients," *The Journal of Urology* 151:1045-1047 (1994).
Davies et al., "Novel 2-Substituted Cocaine Analogs: Binding Properties at Dopamine Transport Sites in Rat Striatum," *European Journal of Pharmacology—Molecular Pharmacology Section* 244:93-97 (1993).
Deckers, "The Chemistry of New Derivatives of Tropane Alkaloids and the Pharmacokinetics of a New Quaternary Compound," *Postgraduate Medical Journal* 51(Suppl. 7):76-81 (1975).
Delforge et al., "Noninvasive Quantification of Muscarinic Receptors In Vivo With Positron Emission Tomography in the Dog Heart," *Circulation* 82(4):1494-1504 (1990).
Delforge et al., "Quantification of Myocardial Muscarinic Receptors with PET in Humans," *The Journal of Nuclear Medicine* 34(6):981-991 (1993).
Ehlert et al., "The Quaternary Transformation Products of N-(3-Chloropropyl)-4-Piperidinyl Diphenylacetate and N-(2-Chloroethyl)-4-Piperidinyl Diphenylacetate (4-DAMP Mustard) Have Differential Affinity for Subtypes of the Muscarinic Receptor," *The Journal of Pharmacology and Experimental Therapeutics* 276(2):405-410 (1996).
Gibson et al., "The Distribution of the Muscarinic Acetylcholine Receptor Antagonists, Quinuclidinyl Benzilate and Quinuclidinyl Benzilate Methiodide (both tritiated), in Rat, Guinea Pig, and Rabbit," *The Journal of Nuclear Medicine* 20(8):865-870 (1979).
Goldstein et al., "Principles of Drug Action: The Basis of Pharmacology," Second Edition, New York: John Wiley & Sons, pp. 22-32 (1974).

Gordon et al., "Distance Geometry of α-Substituted 2,2-Diphenylpropionate Antimuscarinics," *Molecular Pharmacology* 36:766-772 (1989).

Griffin et al., "Kinetics of Activation and In Vivo Muscarinic Receptor Binding of N-(2-Bromoethyl)-4-Piperidinyl Diphenylacetate: An Analog of 4-DAMP Mustard," *The Journal of Pharmacology and Experimental Therapeutics* 266(1):301-305 (1993).

Gross, "Medical Intelligence Drug Therapy. Ipratropium Bromide," *The New England Journal of Medicine* 319:486-494 (1988).

Guan et al., "A Minipig Model for Urodynamic Evaluation of Infravesical Obstruction and its Possible Reversibility," *The Journal of Urology* 154:580-586 (1995).

Haeusler et al., "Drug Therapy of Urinary Urge Incontinence: A Systematic Review," *Obstetrics & Gynecology* 200(5):1003-16 (2002).

Kaiser et al., "Synthesis and Antimuscarinic Properties of Some N-Substituted 5-(Aminomethyl)-3,3-diphenyl-2(3H)-Furnanones," *J. Med. Chem.* 35:4415-4424 (1992).

Kaiser et al., "Synthesis and Antimuscarinic Activity of Some 1-Cycloalkyl-1-Hydroxy-1-Phenyl-3-(4-Substituted Piperazinyl)-2-Propanones and Related Compounds," *J. Med. Chem.* 36:610-616 (1993).

Kondo et al., "A Study on the Affinities of Various Muscarinic Antagonists to the Human Detrusor Muscle," *J. Smooth Muscle Res.* 29:63-68 (1993) (abstract in English).

Kondo et al., "Muscarinic Cholinergic Receptor Subtypes in Human Detrusor Muscle Studied by Labeled and Nonlabeled Pirenzepine, AFDX-116 and 4DAMP," *Urol. Int.* 54:150-153 (1995).

Krishnan et al., "A Double-Blind, Randomized, Placebo Controlled, Parallel Group, Multicentre Study of Intravesical Oxybutynin," *Neurourol. & Urodynamics* 15:307-308 (1996) (Abstract #32).

Newberry et al., "Pharmacological Differences Between Two Muscarinic Responses of the Rat Superior Cervical Ganglion In Vitro," *Br. J. Pharmac.* 92:817-826 (1987).

Nordvall et al., "Binding-Site Modeling of the Muscarinic m1 Receptor: A Combination of Homology-Based and Indirect Approaches," *J. Med. Chem.* 36:967-976 (1993).

Parsons et al., "Epithelial Dysfunction in Nonbacterial Cystitis (Interstitial Cystitis)," *The Journal of Urology* 145:732-735 (1991).

Peterson et al., "Mini-Pig Urinary Bladder Function: Comparisons of In Vitro Anticholinergic Responses and In Vivo Cystometry with Drugs Indicated for Urinary Incontinence," *J. Auton. Pharmac.* 10:65-73 (1990).

Roberts et al., "A Pharmacological Study of the Responses Induced by Muscarinic Agonists on the Isolated Superior Cervical Ganglion of the Guinea Pig," *European Journal of Pharmacology* 186:257-265 (1990).

Rzeszotarski et al., "Analogues of 3-Quinuclidinyl Benzilate," *J. Med. Chem.* 25:1103-1106 (1982).

Sebastian et al., "14β-[(p-Nitrocinnamoyl)amino]morphinones, 14β-[(p-Nitrocinnamoyl)amino]-7,8-dihydromorphinones, and Their Codeinone Analogues: Synthesis and Receptor Activity," *J. Med. Chem.* 36:3154-3160 (1993).

Sethia et al., "An Animal Model of Non-Obstructive Bladder Instability," *The Journal of Urology* 143:1243-1246 (1990).

Shishido et al., "Muscarinic Receptor Subtypes and Their Functional Roles in Rat Detrusor Muscle," 26th Meeting of the International Continence Society, in *Neurourol. & Urodynamics* 15:313-314 (1996) (Abstract #36).

Sternbach et al., "Antispasmodics. I. Bicyclic Basic Alcohols," *J. Amer. Chem. Soc.* 74:2215-2218 (1952).

Thomas et al., "Irreversible Effects of 4-Damp Mustard on Muscarinic Receptors In Vivo," *Proc. West Pharmacol Soc.* 35:233-237 (1992).

Waelbroeck et al., "Binding Kinetics of Quinuclidinyl Benzilate and Methylquinuclidinyl Benzilate Enantiomers at Neuronal ($M_1$), Cardiac ($M_2$), and Pancreatic ($M_3$) Muscarinic Receptors," *Molecular Pharmacology* 40:413-420 (1991).

\* cited by examiner

QUATERNARY ANTIMUSCARINIC COMPOUNDS FOR THE TREATMENT OF BLADDER DISEASES

This application claims the benefit of U.S. Provisional Patent Application Ser. No. 60/441,391, filed Jan. 16, 2003.

FIELD OF THE INVENTION

This invention relates to methods of treating bladder disease, particularly urinary incontinence.

BACKGROUND OF THE INVENTION

Urinary incontinence afflicts a large and diverse patient population. The United States Department of Health and Human Services Agency for Health Care Policy and Research (AHCPR) reviewed the literature on the incidence of urinary incontinence, including the clinical, psychological, and social impact of the disorder, as well as monetary costs to society. (*Overview: Urinary Incontinence in Adults, Clinical Practice Guideline Update*; Agency for Health Care Policy and Research, Rockville, Md. (1996) (AHCPR study)). The 1996 AHCPR study estimated that 13 million Americans are incontinent; of these, 11 million are women. One in four women ages 30-59 has experienced an episode of urinary incontinence, and 50% or more of the elderly persons living at home or in long-term care facilities are incontinent. $16.4 billion is spent every year on incontinence-related care: $11.2 billion for community-based programs and at home, and $5.2 billion in long-term care facilities. $1.1 billion is spent every year on disposable products for adults.

Twenty-nine investigators from 10 countries gathered in San Francisco in June, 2003, at an international symposium sponsored by The National Institute of Diabetes and Digestive and Kidney Diseases (NIDDK) to discuss the current understanding of risk factors and treatment outcomes for incontinence in women. (Brown et al., "Proceedings of the National Institute of Diabetes and Digestive and Kidney Diseases International Symposium on Epidemiologic Issues in Urinary Incontinence in Women," *Suppl to American J Obstetrics and Gynecology* 2A (2003) (NIDDK Symposium). The NIDDK Symposium participants revealed the following facts. The estimated cost of incontinence increased by 250% over 10 years, an amount greater than can be accounted for by medical inflation. Other countries are experiencing this phenomenon as well. In Sweden, for example, the cost of incontinence was estimated as 1.8 billion Swedish crowns (1990 SEK, equivalent to $400 million 1995 U.S. dollars). The elderly account for more than two thirds of the cost of incontinence in the U.S., and costs are expected to increase with the increasing proportion of elderly in society.

A multitude of recent publications further highlight the rising cost to society associated with the management of incontinence and other bladder disorders (Hu et al., "Estimated Economic Costs of Overactive Bladder in the United States," *Urology* 61(6):1123-1128 (2003); Shih et al., "Labor Costs Associated with Incontinence in Long-term Care Facilities," *Urology* 62(3) 442-446 (2003); Green et al., "Urinary Incontinence in Subacute Care—A Retrospective Analysis of Clinical Outcomes and Costs," *MJA* 178:550-553 (2003); Franstz et al., "Implementing an Incontinence Management Protocol in Long-Term Care," *J Gerontological Nursing* 29(8):46-53 (2003)).

Contraction of the bladder detrusor muscle is mediated by cholinergic muscarinic receptors. Muscarinic receptors are divisible into several subtypes ($M_1$-$M_5$ for humans, $m_1$-$m_5$ for animals and other cells) that are distinguishable based on binding of selective ligands. These muscarinic receptor subtypes exist in differing concentrations in different tissues (for a detailed description of anticholinergic agents and their use in treating various diseases, see: Foye, W. O., *Principles Of Medicinal Chemistry*, Lea and Febiger, Philadelphia, Pa., pp. 328-348 (1989); Gilman and Goodman, *The Pharmacological Basis of Therapeutics*, $10^{th}$ edition, Hardman et al., eds., McGraw-Hill, Chapter 7, pp. 162-173 (2000)).

The present invention targets muscarinic receptors by administration of novel antimuscarinic agents via a catheter to the bladder to attain prolonged maintenance of bladder control in otherwise incontinent patients while minimizing systemic side effects of the medication.

The drug oxybutinin chloride(4-diethylamino)2-butynyl-cc-cyclohexyl-a-hydroxybenzeneacetate HCl; trade name Ditropan®) is a standard antimuscarinic therapeutic agent for urinary incontinence. Relief of symptoms in neurogenic bladder disorders is thought to result from its combined antimuscarinic, antispasmodic, and local anesthetic activities. However, antimuscarinic medications are associated with side effects, including dry mouth and cognitive impairment, limiting its acceptability to many patients. These side effects are, at least, unpleasant, and may be intolerable when taken in combination with other medications commonly used by the elderly (Hogan D. B., "Revisiting the O Complex: Urinary Incontinence, Delirium and Polypharmacy in Elderly Patients," *Can Med Assoc J.* 157:1071-7 (1997)). In fact, use of oral oxybutynin is frequently discontinued because of the unpleasantness of the side effects (Thuroff et al., "Randomized, Double-Blind, Multicenter Trial on Treatment of Frequency, Urgency and Incontinence Related to Detrusor Hyperactivity: Oxybutynin Versus Propantheline Versus Placebo," *J. Urol.* 145:813-817 (1991)).

For treatment of detrusor overactivity, AHCPR 1992 (since reissued with revisions) recommended oxybutynin at oral doses of 2.5-5 mg/kg, to be taken 3-4 times per day. At the time of agency review, 5 of 6 randomized controlled studies reported superiority of oxybutinin to placebo. One exception was a study of elderly nursing home residents that used less frequent administration of the drug.

The dose-related antimuscarinic side effects of oral oxybutynin include marked xerostomia, dry skin, blurred vision, nausea, and constipation. Severe mouth dryness occurred in 84% of subjects receiving 5 mg/kg four times/day (AHCPR, 1992). Side effects could be minimized by administration of this compound via clean intermittent self-catheterization directly into the bladder (intravesical administration). However, this required at least daily self-catheterization. Better restoration of bladder control required multiple catheter insertions each day. A series of papers reported beneficial effects in different patient groups. The following are representative: Brendler et al., "Topical Oxybutynin Chloride For Relaxation of Dysfunctional Bladders," *J Urol.* 141:1350-1352 (1989); Weese et al., "Intravesical Oxybutynin Chloride: Experience With 42 Patients," *Urology* 41:527-530 (1993); Greenfield et al., "The Use of Intravesical Oxybutynin Chloride in Children with Neurogenic Bladder," *J. Urol.* 146:532-534 (1991); Madersbacher et al., "Control of Detrusor Hyperreflexia by the Intravesical Instillation of Oxybutynine Hydrochloride," *Paraplegia* 29:84-90 (1991).

A double-blind, randomized, placebo-controlled parallel group study of intravesical oxybutynin was reported in which there was some systemic absorption of the drug following intravesical administration, but the incidence of adverse side effects was low (Krishnan, K. R., "A Double-blind, Randomized, Placebo-Controlled Parallel Group, Multicentre Study of Intravesical Oxybutynin," *Neurourol. and Urodyn.* 15:307-308 (1996)). However, the difficulty in patients being able to continue a typical intravesical instillation protocol is illustrated by Weese et al., "Intravesical Oxybutynin Chloride: Experience With 42 Patients," *Urology* 41:527-530 (1993), which reported that instillation of the drug two to three times daily via clean self intermittent catheterization resulted in 21% of the patients dropping out due to inability to tolerate the catheterization or difficulty in retaining the drug solution in the bladder.

U.S. Pat. No. 5,001,160 to McPherson et al. describes antimuscarinic agents for the treatment of neurogenic bladder disease. The compounds disclosed were said to have longer durations of action than older anticholinergic agents such as methantheline and propantheline. The majority of neurogenic bladder patients have spastic or hypertonic conditions. Clinicians generally aim to convert this condition to hypotonia as a way to treat the primary problem of incontinence. Thus, when the condition has been "converted" to hypotonia, it can be managed in a straightforward way by intermittent catheterization. For those patients who cannot be converted from the hypertonic to the hypotonic state and who still need to urinate every hour, longer term treatment with muscarinic receptor antagonists (loosely called anticholinergics) was said to be necessary. As noted above, the current drug of choice for this treatment modality is oxybutynin, which is considered to be better than the older anticholinergics. McPherson et al. disclosed 1-aryl-1-hydroxy-1-R,-3-(4-R,-1-piperazinyl)-2-propanones for treatment of bladder disease (U.S. Pat. No. 5,001,160). In preferred compounds, $R_1$ was a cycloalkyl of 3-6 carbons, most preferably cyclohexyl or cyclobutyl. $R_2$ was lower alkyl, benzyl, para-substituted benzyl or cinnamyl. The most preferred compound was 1-cyclobutyl-1-hydroxy-1-phenyl-3-(4-benzyl-1-piperazinyl)-2-propanone. For parenteral administration, the compounds were prepared in conventional aqueous injection solutions. U.S. Pat. No. 5,001,160 also disclosed that extemporaneous injection solutions could be prepared from sterile pills, granules or tablets, and contained diluents, dispersing and surface active agents, binders, and lubricants, as well as the anticholinergic compound. Tolterodine is a new antimuscarinic of comparable duration of action which is reported to cause a lower incidence of dry mouth (~9%). The following dose-related side effects were observed with tolterodine: diminished stimulated salivation after 3.2 mg, increased heart rate after 6.4 mg, and altered the nearpoint of vision after 12.8 mg. Six of 8 subjects reported micturition difficulties after a dose of 12.8 mg.

Other Drugs in the Treatment of Urinary Incontinence

Terodiline has both anticholinergic and calcium antagonist properties, and effectively reduces abnormal bladder contractions caused by detrusor instability (Langtry et al., "Terodiline. A Review of its Pharmacological Properties, and Therapeutic Use in the Treatment of Urinary Incontinence," *Drugs* 40:748-761(1990)). When administered to adult patients with urge incontinence (generally as a 25 mg dose twice daily), terodiline reduced micturition frequency and incontinence episodes. Bladder volume at first urge and bladder capacity were increased. Children with diurnal enuresis respond similarly to a daily 25 mg dose. Terodiline at 50 mg/day was said to be preferred by patients when compared with emepronium 600 mg/day or flavoxate 600 mg/day, and tended to reduce voluntary micturition frequency and episodes of incontinence more effectively than these other drugs. Anticholinergic side effects were the most common ones reported.

Anhydroecgonine Derivatives as Anticholinergic Agents

Anhydroecgonine methyl ester (AEME), the primary pyrolysis product of cocaine (Martin et al., "Pyrolysis and Volatilization of Cocaine," *J. Anal Toxicol* 13:158-162 (1989)), is structurally similar to arecoline and anatoxin A. While investigating the effects of crack smoking, it was noted that experimental animals frequently showed bronchoconstriction (Wood et al., "Generation of Stable Test Atmospheres of Cocaine Base and Its Pyrolyzate, Methylecgonidine, and Demonstration of Their Biological Activity," *Pharmacology, Biochemistry & Behavior* 55(2):237-48 (1996); Chen et al., "Pulmonary Effects of the Cocaine Pyrolysis Product, Methylecgonidine, in Guinea Pigs," *Life Sciences* 56(1):7-12 (1995)).

This observation led to a focus on AEME and other anhydroecgonine esters (AEE) as bronchoconstrictors when given by inhalation. When this agent was studied in isolated guinea pig tracheal rings, it was found unexpectedly (in view of the bronchoconstricting action of cocaine), that AEME lacked cholinergic agonist activity in this tissue and in detrusor muscle in vitro. Subsequently, some agonistic effects were demonstrated at high doses in sheep consistent with action at the $M_2$ muscarinic receptors.

Even more surprisingly, AEME turned out to be a potent non-competitive muscarinic antagonist in vitro (El-Fawal et al., "Airway Smooth Muscle Relaxant Effects of the Cocaine Pyrolysis Product, Methylecgonidine," *J Pharm Exp Ther* 272:991-996 (1995)).

The antagonistic effects were insurmountable even with the addition of increasing amounts of acetylcholine (ACh). Furthermore, the anticholinergic effects were irreversible, so that tissue exposed to AEME could not later attain its original magnitude of contraction. These in vitro findings were unexpected because AEME, resembling arecoline and anatoxin in structure, was expected to behave as a cholinergic agonist. AEE compositions, derivatives or analogues thereof having anticholinergic activity, methods of preventing or inhibiting cholinergic responses, and methods of using the compositions to prevent or treat diseases associated with bronchoconstriction have been described (U.S. Pat. Nos. 5,552,407 and 5,821,249 to Wood et al.).

Note that some effects were subsequently demonstrated at high doses of this interesting compound that are consistent with agonist activity at the $m_2$ muscarinic receptor in sheep (Scheidweiler et al., "Pharmacokinetics and Pharmacodynamics of Methylecgonidine, a Crack Cocaine Pyrolyzate," *J Pharm Exp Ther* 307:1179-1187 (2003)), as well as effects in guinea pigs (Willetts et al., "Effects of Methylecgonidine on Acetylcholine-Induced Bronchoconstriction and Indicators of Lung Injury in Guinea Pigs," *Life Sciences* 57(15):225-30 (1995)).

Other Bladder Diseases

Interstitial cystitis (IC), a syndrome occurring primarily in women, is characterized by urinary urgency and frequency, suprapubic pain, and petechial bladder mucosal hemorrhages upon distention under general anesthesia. Almost 50% of IC patients also suffer from allergies and irritable bowel syndrome, all of which are exacerbated by stress. One of the prevailing theories to explain IC pathophysiology is the increased number of activated mast cells in the bladder. Mast cells mediate hypersensitivity reactions wherein they are triggered by immunoglobulin E (IgE) and antigen (allergen) to release numerous vasoactive anproinflammatory substances. Mast cells are found in juxtaposition to neurons and are also activated by direct nerve stimulation, as well as by ACh, neurotensin, and Substance P. Barbalias, G A, "Interstitial Cystitis: Bladder Training with Intravesical Oxybutynin," *J.*

*Urol.* 163:1818-1822 (2000), demonstrated that intravesical administration of oxybutynin to women with interstitial cystitis resulted in an improvement in their signs and symptoms that was better than the improvement produced by simple expansion of the bladder with saline.

Targeting Parasympathetic Control of Organ Function

In addition to its role in bladder control, the parasympathetic nervous system plays a major role in regulating bronchomotor tone. One drug used to treat respiratory disease, such as asthma, is the quaternary anticholinergic agent isopropylatropine bromide, also called ipratropium bromide (Atrovent®) (Gross, H. J., "Ipratropium Bromide," *New Eng. J. Med.* 319:486-494 (1988); "Anticholinergic Therapy: The State of the Art. Proceedings of a Symposium Held in Stratford-Upon Avon 8-9 Sep. 1986," Higgenbottam et al, eds., *Postgrad. Med. J.* 63 (Suppl 1): 1-93 (1987)). This agent, administered by inhalation, is poorly absorbed so that it exerts its effects primarily, and in a limited manner, on the internal surfaces of the lungs. Thus, a major advantage of ipratropium for respiratory therapy is the possibility of reaching elevated regional tissue (e.g., lung) concentrations with few systemic anticholinergic effects. Another advantage of ipratropium compared to other anti-asthmatic drugs is its duration of action. Its pharmacologic effect becomes maximal in about an hour, and persists for several hours. A compound with these features may also be useful for long duration therapy of bladder disease.

Thus, antimuscarinic therapies are widely used for treatment of bladder diseases, but they are fraught with side effects, which not only limit their acceptance by patients, but also complicate medical management. What are needed are effective methods of treating bladder disease without the unpleasant side effects associated with the current standard therapeutics.

SUMMARY OF THE INVENTION

The present invention relates to a method for treating bladder disease in a subject. This method involves administering to a subject a pharmaceutical composition having a therapeutic amount of a compound selected from the group consisting of: (1) a compound having the formula

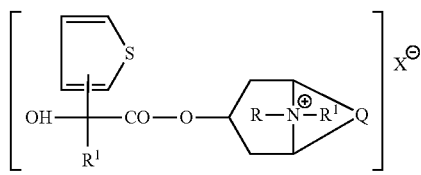

where Q is a group of the formula

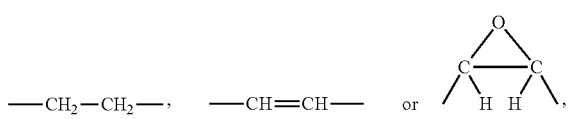

R and $R^1$ are each independently $C_1$-$C_4$-alkyl, $R_1$ is thienyl, phenyl, cyclopentyl or cyclohexyl, and $X^-$ is a physiologically acceptable anion; (2) a compound having the formula

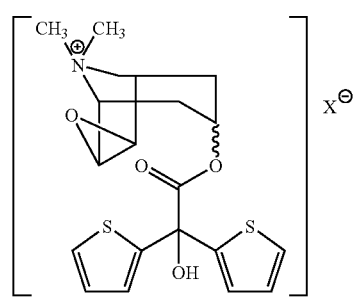

where $X^-$ is a physiologically acceptable ion; (3) a compound having the formula

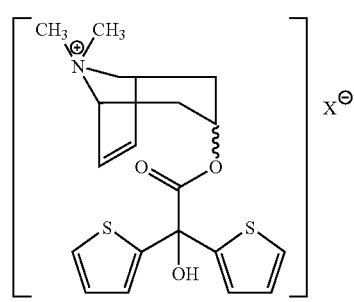

where $X^-$ is a physiologically acceptable ion; (4) a compound having the formula

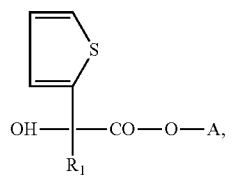

where $R_1$ is 2-thienyl or cyclopentyl, and A is 3α-(6,7-dehydro)-tropanyl methobromide, 3β-tropanyl methobromide, or 3α-(N-isopropyl)-nortropanyl methobromide; (5) a compound having the formula

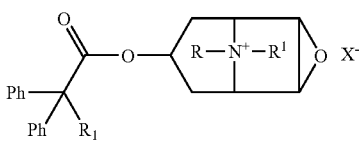

where R is an optionally halo- or hydroxyl-substituted $C_{1-4}$ alkyl group, $R^1$ is a $C_{1-4}$-alkyl group, or R and $R^1$ together form a $C_{4-6}$-alkylene group, $X^-$ is a physiologically acceptable anion, and $R_1$ is H, OH, $CH_3$, $CH_2OH$, $C_{1-4}$ alkyl or $C_{1-4}$-alkoxy; (6) a compound having the formula

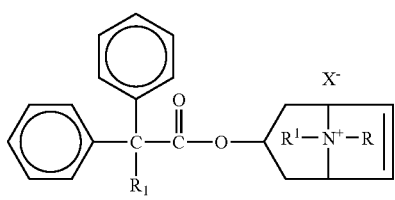

where R is an optionally halo- or hydroxy-substituted $C_{1-4}$-alkyl group, $R^1$ is a $C_{1-4}$-alkyl group, or R and $R^1$ together form a $C_{4-6}$-alkylene group, $X^-$ is a physiologically acceptable anion and $R_1$ is H, OH, $CH_3$, $CH_2OH$, $C_{1-4}$-alkyl or $C_{1-4}$-alkoxy; (7) a compound having the formula

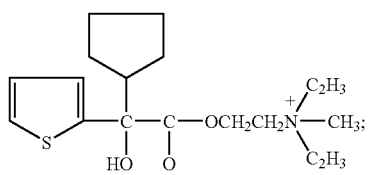

(8) a compound having the formula

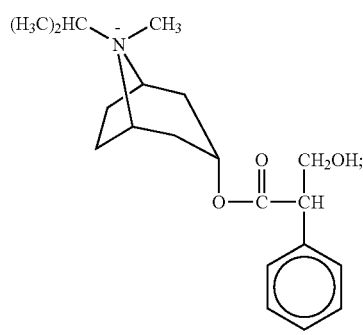

and (9) a compound having the formula

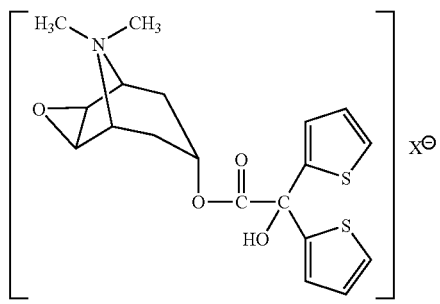

where $X^-$ is a physiologically acceptable anion.

The administration of antimuscarinic agents, often called anticholinergics in clinical medicine, with prolonged duration of action via a catheter to the bladder, results in prolonged maintenance of bladder control in otherwise incontinent patients. Agents with durations of action between a week and a month could be useful for a significant number of patients and perhaps reach distinct groups for whom no satisfactory treatment is currently available. In addition, a goal of drug research in the field of urinary incontinence has been to develop or identify long-acting antimuscarinic agents for the control of overactive bladder, detrusor instability, and urge incontinence that are free of side effects such as dry mouth and cognitive impairment. Standard antimuscarinic medications for the treatment of detrusor instability or urge incontinence produce side effects that may be intolerable, particularly when taken in combination with other medications commonly used by the elderly. The present invention is directed to overcoming these and other deficiencies in the art.

DETAILED DESCRIPTION OF THE INVENTION

The present invention relates to a method for treating bladder disease in a subject. This method involves administering to a subject a pharmaceutical composition having a therapeutic amount of a compound selected from the group consisting of: a compound having the formula

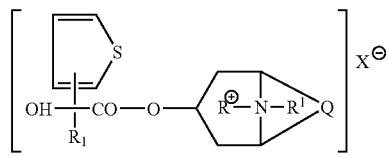

where Q is a group of the formula

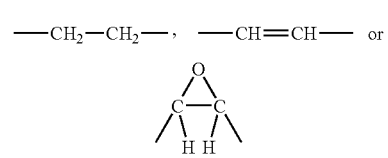

R and $R^1$ are each independently $C_1$-$C_4$-alkyl, $R_1$ is thienyl, phenyl, cyclopentyl or cyclohexyl, and $X^-$ is a physiologically acceptable anion. In this aspect and all aspects of the present invention, R may be, without limitation, $CH_3$, $C_2H_5$, n-$C_3H_7$, or i-$C_3H_7$; $R^1$ may be, without limitation, $CH_3$, and $X^-$ is meant to include, without limitation, bromide ($Br^-$) and $CH_3SO_3$.

In another aspect of the present invention, treatment of a bladder disease involves administering to a subject a compound having the formula

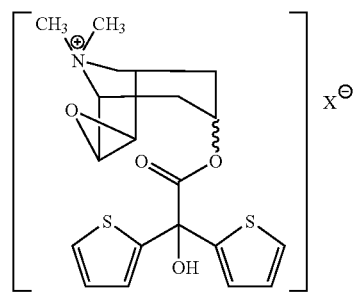

where $X^-$ is a physiologically acceptable ion as described herein above.

In another aspect of the present invention, treatment of a bladder disease involves administering to a subject a compound having the formula

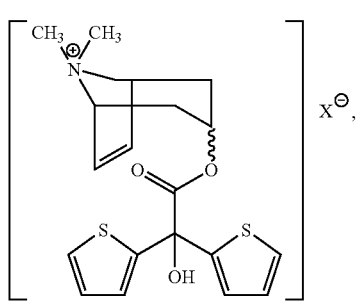

where X— is a physiologically acceptable ion as described above.

In another aspect of the present invention, treatment of a bladder disease involves administering to a subject a compound having the formula

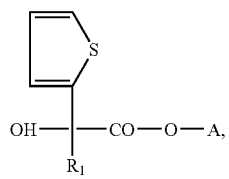

where $R_1$ is 2-thienyl or cyclopentyl, and A is 3α-(6,7-dehydro)-tropanyl methobromide, 3β-tropanyl methobromide, or 3α-(N-isopropyl)-nortropanyl methobromide.

In another aspect of the present invention, treatment of a bladder disease involves administering to a subject a compound having the formula

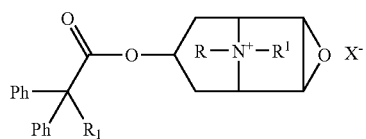

where R is an optionally halo- or hydroxyl-substituted $C_{1-4}$ alkyl group, $R^1$ is a $C_{1-4}$ alkyl group, or R and $R^1$ together form a $C_{4-6}$-alkylene group, $X^-$ is a physiologically acceptable ion as described herein above, and $R_1$ is H, OH, $CH_2OH$, $C_{1-4}$ alkyl or $C_{1-4}$ alkoxy.

In another aspect of the present invention, treatment of a bladder disease involves administering to a subject a compound having the formula

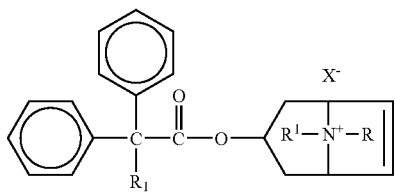

where R is an optionally halo- or hydroxyl-substituted $C_{1-4}$ alkyl group, $R^1$ is a $C_{1-4}$ alkyl group, or R and $R^1$ together form a $C_{4-6}$-alkylene group, $X^-$ is a physiologically acceptable ion as described herein above, and $R_1$ is H, OH, $CH_2OH$, $C_{1-4}$ alkyl or $C_{1-4}$ alkoxy.

In another aspect of the present invention, treatment of a bladder disease involves administering to a subject a compound having the formula:

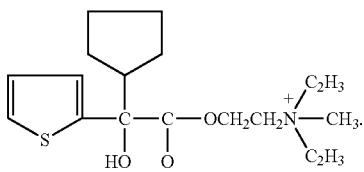

In another aspect of the present invention, treatment of a bladder disease involves administering to a subject a compound having the formula

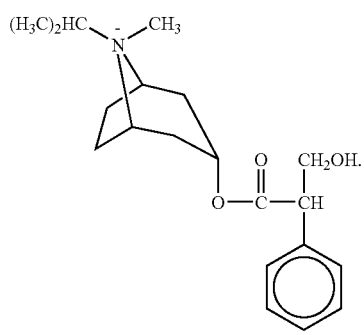

In another aspect of the present invention, treatment of a bladder disease involves administering to a subject a compound having the formula

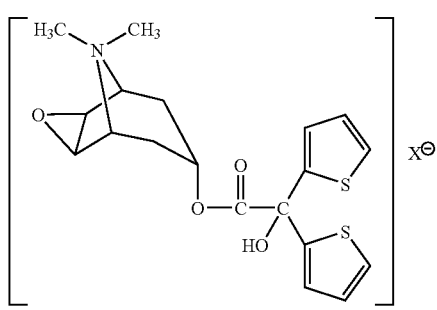

where $X^-$ is a physiologically acceptable ion as described herein above.

These compounds are described in further detail in U.S. Pat. Nos. 5,610,163, 5,654,314, and 5,770,738 to Banholzer et al., which are hereby incorporated by reference in their entirety.

An exemplary compound for use in the method of the present invention is tiotropium bromide (6β,7β,Epoxy-3α-[2-hydroxy-2,2-di(2-thienyl)acetoxy]-8,8-dimethyl-1αH, 5αH-tropanium bromide) (Norman et al., "Tiotropium Bromide, Treatment of COPD Bronchodilator Muscarinic Antagonist," *Drugs of the Future* 25(7):693-699 (2000), which is hereby incorporated by reference in its entirety). This new generation compound has been shown to have unique pharma, exhibiting a specific highly potent antagonism at all subtypes of human muscarinic receptors in the 10-11 M range in vitro (KD-value from kinetic measurements at $M_3$: 14 pM) (Disse et al., "Ba 679 BR, A Novel Long- Acting Anticholinergic Bronchodilator," *Life Sci* 52(5-6): 537-44 (1993); Disse et al., "Tiotropium (Spiriva): Mechanistical Considerations and Clinical Profile in Obstructive Lung Disease," *Life Sci* 4(6-7):457-64 (1999), which are hereby incorporated by reference in their entirety), but its special characteristic is its slow dissociation from $M_3$-receptors (half-life of 35 hours) as compared to 16 minutes for ipratropium. This is indicative of a long duration of action effected by prolonged receptor binding and not by long residence time in plasma or tissue compartments. Tiotropium, similar to ipratropium, is in the classical view not subtype-selective (based on similar KD values at muscarinic receptor subtypes). However, tiotropium dissociation from $M_2$ (3.6 hours) is faster than from $M_3$-receptors (35 hours) which, in functional experiments, is manifest as a "kinetic type" of receptor subtype selectivity of $M_3$ (and $M_1$) over $M_2$ receptors (Takahashi et al., "Effect of Ba 679 BR, A Novel Long-Acting Anticholinergic Agent, On Cholinergic Neurotransmission in Guinea Pigs and Human Airways," *Am J Resp Crit Care Med* 150:1640-1645 (1994), which is hereby incorporated by reference in its entirety).

Both enantiomers of the compounds and racemic mixtures are understood to be suitable for use in the present invention.

The preferred route of administration for treatment is intravesical, although oral or systemic routes might be effective if controlled release within the bladder could be achieved with further pharmaceutical development effort.

Methods for intravesical administration of medications to the bladder are well-known, as are methods for testing the efficacy of compounds for the treatment of disease. For example, publications are available that teach intravesical delivery and testing methods (Wood et al., "Automated Noninvasive Measurement of Cyclophosphamide-Induced Changes in Murine Voiding Frequency and Volume," *J Urol.* 165:653-659 (2001); Eichel et al., "Assessment of Murine Bladder Permeability with Fluorescein: Validation With Cyclophosphamide and Protamine," *Urology* 58(1):113-118 (2001); Sessions et al., "Continuous Bladder Infusion Methods for Voiding Function in the Ambulatory Mouse," *Urology* 60(4):707-713 (2002); which are hereby incorporated by reference in their entirety); uroflow measurement methodologies (Wood et al., "Uroflow in Murine Urethritis," Abstract, *Research Insights into Interstitial Cystitis: A Basic and Clinical Science Symposium*, Oct. 30-Nov. 1, 2003, Alexandria Va.; co-presented by the National Institute of Diabetes and Digestive and Kidney Diseases and the Interstitial Cystitis Association, which is hereby incorporated by reference in its entirety); and the assessment of the efficacy and location of the peripheral (i.e., non-CNS) effect of a test compound (U.S. Pat. No. 6,573,282 to Yaksh et al., which is hereby incorporated by reference in its entirety).

A wide variety of patient populations may benefit from these medications, especially those with urge and frequency incontinence, detrusor instability, and detrusor-external sphincter dyssynergia. A non-exclusive list of exemplary conditions to which the present invention is suitable include: urge incontinence, cystitis (including interstitial cystitis), bladder dysfunction of multiple sclerosis, benign prostatic hyperplasia, myelomeningocele (spina bifida), spinal cord injury, patients with dementias for whom antimuscarinic medications are contraindicated, parkinsonism, and patients who cannot tolerate systemic effects of antimuscarinic medications because of concurrent medication with other agents or because of blurred vision, dry mouth, constipation, cognitive impairment or other sequelae of antimuscarinic medications.

The present invention relates to a method for treating bladder disease comprising administering an antimuscarinic agent or a derivative or analogue thereof as described above in a pharmaceutically acceptable carrier or excipient for intravesical instillation. Preferred additions to such compositions are materials which enhance viscosity or promote the entry of the active agent into the bladder wall, including carboxymethyl celluloses, glycosaminoglycans (GAGs), pentosan polysulfate, heparin, or heparin-like compounds. In one aspect of the present invention, the treatment includes the physical or pharmacological creation of a depot/slow release compartment for the composition. This can be achieved, for example, by delivery of the agent using liposomes or other known delivery agents having the noted action on release. Another approach involves the use of protamine (or a protamine-like compound) to alter the surface of the bladder, thereby fostering access or to enhance access. The subject is first treated with protamine or a protamine-like agent, followed by administration of the active antimuscarinic agent in combination with a glycosoaminoglycans.

In another aspect of the present invention, the endogenous intravesical GAG compartment is exchanged with, or replaced by, an exogenously applied mixture that incorporates the antimuscarinic composition of this invention. Suitable additions would also include those which would provide the formulation with a longer mechanical presence in the bladder, allowing the compound of the present invention to diffuse from the bladder tissue, find a site on the bladder wall, or enhance the ability of the compound to infiltrate the tissue, and/or provide a slow release of existing pools of drug from the tissue.

Considering the spectrum of potential side effects of agents with irreversible or very long duration activities, the prevention of central nervous system (CNS) effects emerges as a significant priority, as one would not want a chronic impairment of memory or cognition in an elderly population. Thus, quaternary amino compounds emerge as the most preferred in this regard. Quaternary antimuscarinic compounds have achieved clinical use. Quaternary compounds have long been used in experimental pharmacology to distinguish central from peripheral mechanisms of actions. For example, methylatropine and methylscopolamine retain their peripheral anticholinergic activities, but do not affect conditioned behaviors as effectively as do atropine or scopolamine molecules.

For use in accordance with this invention, the preferred antimuscarinic agent has (1) receptor-selective activity, and (2) the activity is of long duration in the target organ following local administration to an internal surface of that organ. An example from the art of treating asthma is the local application of isopropylatropine to the inner surface of the lung. If the agent is not given in excess dosage, long duration side effects should not occur. Quaternization does not eliminate peripheral activity; one of the primary purposes of this chemical change is to prevent passage of the agent across the blood-brain barrier. There are no known publications describing the effect of quaternization of a compound administered intravesically on subsequent blood levels of the quaternary compound. There is an expectation of some systemic absorption. The main consequence of overdose via the intravesical route is most likely to be hypotonicity of the bladder detrusor muscle. This side effect would be counteracted by clean intermittent or subchronic catheterization until the effect diminishes. No significant peripheral side effects in the presence of drug-induced detrusor hypotonicity are expected. Nonetheless, chemical modifications of the antimuscarinic agent to exclude it from the central nervous system is desirable in the context of chronic use; if the usual anticholinergic peripheral side effects did occur, they might be unpleasant but would not result in subtle or serious central nervous system impairment.

An agent may achieve long duration of action by having high affinity for, or slow off-rates from, the receptor responsible for its clinically useful effect. Alternatively, the agent may be retained in the body for a prolonged period of time, or differentially partition into or be retained within a compartment of the body in which the agent exerts its desirable effects. The urothelium is lined with glycoprotein and glycosaminoglycan structures that present a negative charge to the lumen of the bladder; one consequence is the ordering of water molecules into layers at the bladder surface, a phenomenon that may play a role in urothelial barrier function. Since intravesically administered quaternary agents have a positive charge, they may be electrostatically attracted to this surface where they may bind. In so doing they may be held in proximity to the site of action of the compound, resulting in a prolongation of their duration of action.

As used in the present invention, "antimuscarinic" is interchangeable with "anticholinergic." Acetylcholine is a flexible compound that changes in length and therefore the same compound (in different conformations) fits nicotinic and muscarinic acetylcholine receptors. As used in the art, in particular when describing atropine-like drugs such as ipratropium, both anticholinergic and antimuscarinic are correct, the latter being preferred by the pharmacologic purist (Witek, T. J. Jr., "Anticholinergic Bronchodilators," *Respiratory Clinica of North America* 5:521-536 (1999), which is hereby incorporated by reference in its entirety).

According to the present invention, a composition used to treat bladder disease is preferably substantially irreversible, meaning that it has a prolonged duration of action compared to a conventional muscarinic antagonist. This may be a result of covalent bonding to a receptor or another site of the cell, or because of a slow "off rate". This term is not intended to imply that one cannot measure an "off rate" (as in the case of hydrolysis of a xenobiotic where the receptor is left in a free state). To be substantially irreversible as intended herein, a compound preferably has a duration of pharmacologic effect of at least 12 hours, more preferably at least 24 hours, more preferably at least 7 days, even more preferably at least about 3 weeks. The desired pharmacologic effect is that of increased residual bladder volume and/or reduced peak intravesical pressure, leading to the prevention of unwanted episodes of micturition. As is well-known in the pharmacologic arts, termination of an agent's action may result from a number of processes including tolerance of the subject, dissociation from the receptor, receptor upregulation, breakdown of the agent in situ, and the associated return of the receptor to the functional population.

The criteria for the inclusion of a compound in the present invention are its ability to mimic the actions of an anticholinergic drug, such as oxybutynin, but with a longer duration of action. The compounds of this invention must have an action that results in one or, preferably, a combination, of the following outcomes: (1) decreased peak intravesical pressure during voiding; (2) increased bladder capacity; (3) increased interval between voids. Furthermore, the compound should have few side effects and be well-tolerated by patients. Side effects are minimized in several ways, compared to drugs in the prior art. First, intravesical administration, the preferred route, itself results in fewer systemic effects than systemic administration of the drug.

The presence of a quaternary nitrogen atom, a high degree of lipophilicity, a bulky side chain or other means for increasing the overall size and molecular mass of the pharmacologically active moiety, or a combination of these properties, minimizes entry into the CNS, thereby avoiding a significant number of known side effects.

As used herein, "alkyl" or "alkylene" is intended to include both branched and straight-chain aliphatic hydrocarbon groups having a specified number of carbon atoms. Examples of alky groups include, but are not limited to, methyl, ethyl, n-propyl, i-propyl, n-butyl, i-butyl, sec-butyl, t-butyl, pentyl, and hexyl.

"Alkoxy" or "alkyloxy" as used herein represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" as used herein represents an alkyl group as defined above with the indicated number of carbon atoms attached through a sulphur bridge.

As used herein, "pharmaceutically acceptable ions" refers to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, without limitation, those derived from inorganic acids including hydrochloric, hydrobromic, sulfuric, sulfamic, phosphoric, nitric, and the like; and the salts prepared from organic acids including, without limitation, acetic, propionic, succinic, glycolic, stearic, lactic, malic, tartaric, citric, ascorbic, palmist, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's *Pharmaceutical Sciences,* 17th ed., p. 1418, Mack Publishing Company, Easton, Pa. (1985), which is hereby incorporated by reference in its entirety.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for treating urge incontinence in a subject, said method comprising:
    administering intravesically to the subject a pharmaceutical composition comprising:
    a therapeutic amount of a compound selected from the group consisting of: (1) a compound having the formula

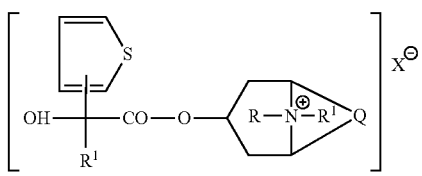

wherein Q is a group of the formula

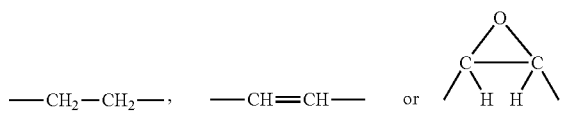

R and R¹ are each independently $C_1$-$C_4$-alkyl, $R_1$ is thienyl, phenyl, cyclopentyl or cyclohexyl and X⁻ is a physiologically acceptable anion; (2) a compound having the formula

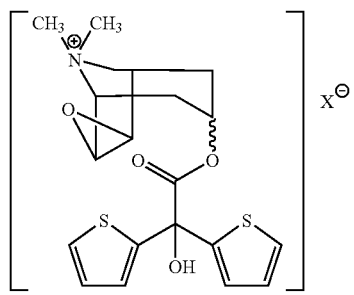

wherein X⁻ is a physiologically acceptable ion; (3) a compound having the formula

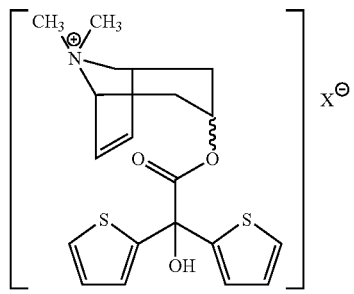

wherein X⁻ is a physiologically acceptable ion; (4) a compound having the formula

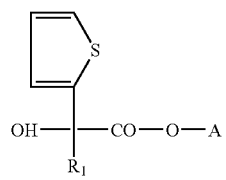

wherein $R_1$ is 2-thienyl or cyclopentyl, and A is 3α-(6,7-dehydro)-tropanyl methobromide, 3β-tropanyl methobromide, or 3α-(N-isopropyl)-nortropanyl methobromide; (5) a compound having the formula

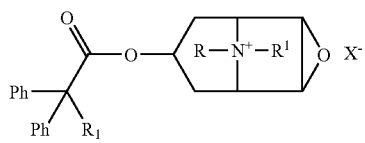

wherein R is an optionally halo- or hydroxyl-substituted $C_{1-4}$ alkyl group, R¹ is a $C_{1-4}$ alkyl group, or R and R¹ together form a $C_{4-6}$ alkylene group; X⁻ is a physiologically acceptable anion, and $R_1$ is H, OH, $CH_2OH$, $C_{1-4}$ alkyl or $C_{1-4}$ alkoxy; (6) a compound having the formula

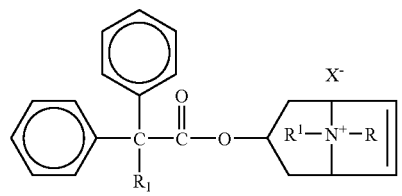

wherein R is an optionally halo- or hydroxy-substituted $C_{1-4}$-alkyl group, R¹ is a $C_{1-4}$-alkyl group, or R and R¹ together form a $C_{4-6}$-alkylene group, X⁻ is a physiologically acceptable anion and $R_1$ is H, OH, $CH_3$, $CH_2OH$, $C_{1-4}$-alkyl, or $C_{1-4}$-alkoxy; (7) a compound having the formula

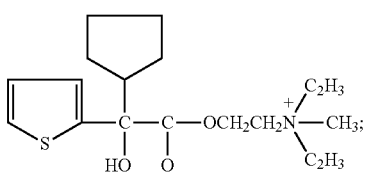

(8) a compound having the formula

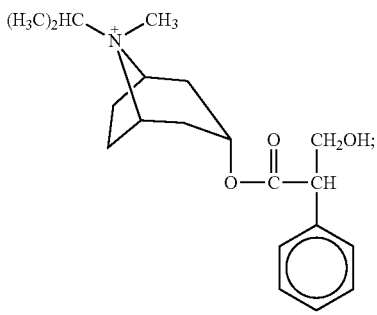

and (9) a compound having the formula

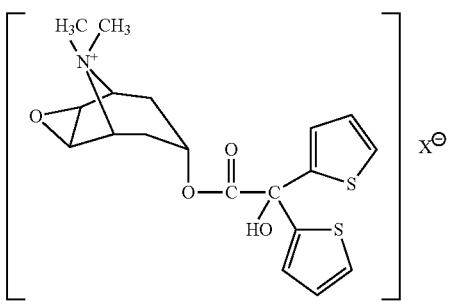

wherein X⁻ is a physiologically acceptable anion and
an additive which enhances adherence of said compound to the subject's bladder-wall and prolongs duration of action compared to when the compound is not in a composition containing the additive.

2. The method according to claim 1, wherein the compound has the formula

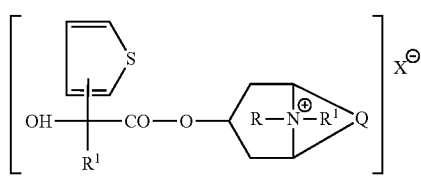

wherein Q is a group of the formula

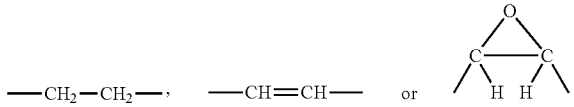

R and $R^1$ are each independently $C_{1-4}$-alkyl, $R_1$ is thienyl, phenyl, cyclopentyl or cyclohexyl, and X⁻ is a physiologically acceptable anion.

3. The method according to claim 2, wherein R is $CH_3$, $C_2H_5$, n-$C_3H_7$, or i-$C_3H_7$ and $R^1$ is $CH_3$.

4. The method according to claim 3, wherein $R_1$ is thienyl.

5. The method according to claim 2, wherein X⁻ is Br⁻ or $CH_3SO_3$.

6. The method according to claim 1, wherein the compound has the formula

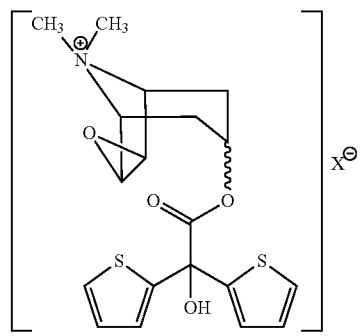

wherein X⁻ is a physiologically acceptable ion.

7. The method according to claim 1, wherein the compound has the formula

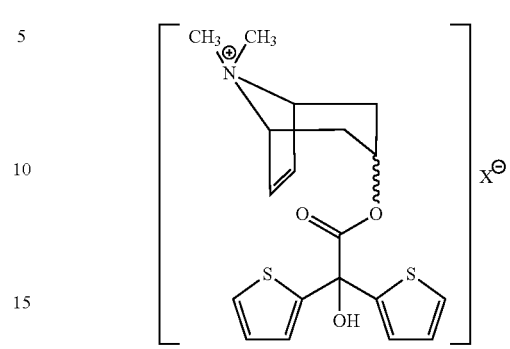

wherein X⁻ is a physiologically acceptable ion.

8. The method according to claim 1, wherein the compound has the formula

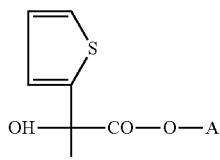

$R_1$ is 2-thienyl or cyclopentyl, and A is 3α-(6,7-dehydro)-tropanyl methobromide, 3β-tropanyl methobromide, or 3α-(N-isopropyl)-nortropanyl methobromide.

9. The method according to claim 8, wherein $R_1$ is 2-thienyl and A is 3α-(6,7-dehydro)-tropanyl methobromide.

10. The method according to claim 8, wherein $R_1$ is 2-thienyl and A is 3β-tropanyl methobromide.

11. The method according to claim 8, wherein $R_1$ is cyclopentyl and A is 3α-(N-isopropyl)-nortropanyl methobromide.

12. The method according to claim 1, wherein the compound has the formula

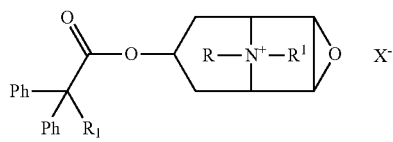

wherein R is an optionally halo- or hydroxyl-substituted $C_{1-4}$ alkyl group, $R^1$ is a $C_{1-4}$ alkyl group, or R and $R^1$ together form a $C_{4-6}$ alkylene group; X⁻ is a physiologically acceptable anion, and $R_1$ is H, OH, $CH_3$, $CH_2OH$, $C_{1-4}$ alkyl or $C_{1-4}$ alkoxy.

13. The method according to claim 12, wherein X⁻ is bromide.

14. The method according to claim 12, wherein $R_1$ is OH, $CH_3$, or $CH_2OH$.

15. The method according to claim 12, wherein R is methyl and $R^1$ is methyl, ethyl, n-propyl or i-propyl.

16. The method according to claim 1, wherein the compound has the formula

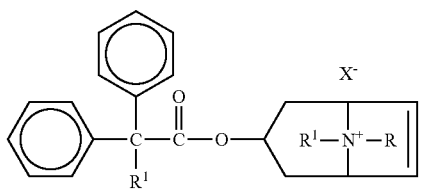

wherein R is an optionally halo- or hydroxy-substituted $C_{1-4}$-alkyl group, $R^1$ is a $C_{1-4}$-alkyl group, or R and $R^1$ together form a $C_{4-6}$-alkylene group, $X^-$ is a physiologically acceptable anion and $R_1$ is H, OH, $CH_2OH$, $C_{1-4}$-alkyl, or $C_{1-4}$-alkoxy.

17. The method according to claim 16, wherein $X^-$ is bromide.
18. The method according to claim 16, wherein $R_1$ is OH, $CH_3$, or $CH_2OH$.
19. The method according to claim 16, wherein R is methyl and $R^1$ is methyl, ethyl, n-propyl or i-propyl.
20. The method according to claim 1, wherein the compound has the formula

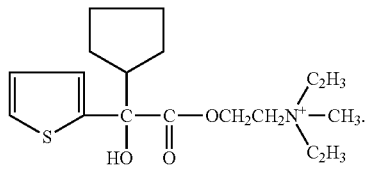

21. The method according to claim 1, wherein the compound has the formula

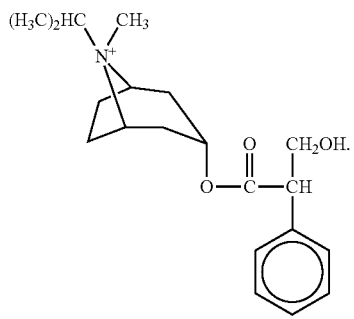

22. The method according to claim 1, wherein the compound has the formula

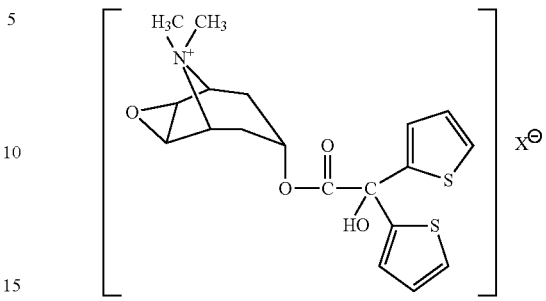

wherein $X^-$ is a physiologically acceptable anion.

23. The method according to claim 22, wherein $X^-$ is a bromide.
24. The method according to claim 1, wherein the prolonged duration of action is at least about three weeks.
25. The method according to claim 1, wherein the additive is selected from the group consisting of carboxymethyl celluloses, glycosaminoglycans, pentosan polysulfate, and heparin.
26. The method according to claim 1, wherein the additive enhances viscosity or promotes entry into or adherence of the compound to the bladder wall.
27. The method according to claim 1, wherein the additive is a liposome in which the compound is contained.
28. The method according to claim 1, wherein the additive alters the surface of the bladder to foster and/or enhance access of the compound to the bladder.
29. The method according to claim 1, wherein the additive is a protamine.
30. The method according to claim 26, wherein the additive enhances viscosity of the compound.
31. The method according to claim 26, wherein the additive promotes entry of the compound into the bladder wall.
32. The method according to claim 26, wherein the additive promotes adherence of the compound to the bladder wall.

* * * * *